US012594316B2

(12) United States Patent
Su et al.

(10) Patent No.: US 12,594,316 B2
(45) Date of Patent: *Apr. 7, 2026

(54) PLANT COMPOSITION, TRADITIONAL CHINESE MEDICINE COMPOSITION AND USE THEREOF

(71) Applicant: NATIONAL RESEARCH INSTITUTE OF CHINESE MEDICINE, MINISTRY OF HEALTH AND WELFARE, Taipei City (TW)

(72) Inventors: Yi-Chang Su, Taipei City (TW); Wen-Hui Chiou, Taipei City (TW); Yuh-Chiang Shen, Taipei City (TW); Wen-Chi Wei, Taipei City (TW); Keng-Chang Tsai, Taipei City (TW); Chia-Ching Liao, Taipei City (TW); Yu-Hwei Tseng, Taipei City (TW); Chun-Tang Chiou, Taipei City (TW); Yu-Chi Lin, Taipei City (TW); Li-Hsiang Wang, Taipei City (TW)

(73) Assignee: National Research Institute of Chinese Medicine, Ministry of Health and Welfare, Taipei City (TW)

( * ) Notice: Subject to any disclaimer, the term of this patent is extended or adjusted under 35 U.S.C. 154(b) by 636 days.

This patent is subject to a terminal disclaimer.

(21) Appl. No.: 18/047,697

(22) Filed: Oct. 19, 2022

(65) Prior Publication Data

US 2023/0124965 A1 Apr. 20, 2023

Related U.S. Application Data

(60) Provisional application No. 63/262,793, filed on Oct. 20, 2021.

(51) Int. Cl.
| | |
|---|---|
| *A61K 36/00* | (2006.01) |
| *A61K 36/076* | (2006.01) |
| *A61K 36/282* | (2006.01) |
| *A61K 36/428* | (2006.01) |
| *A61K 36/539* | (2006.01) |
| *A61K 36/575* | (2006.01) |
| *A61K 36/704* | (2006.01) |
| *A61K 36/714* | (2006.01) |
| *A61K 36/78* | (2006.01) |
| *A61K 36/8888* | (2006.01) |
| *A61K 36/8969* | (2006.01) |
| *A61P 11/00* | (2006.01) |
| *A61P 31/14* | (2006.01) |
| *A61K 36/484* | (2006.01) |

(52) U.S. Cl.
CPC .......... *A61K 36/714* (2013.01); *A61K 36/076* (2013.01); *A61K 36/282* (2013.01); *A61K 36/428* (2013.01); *A61K 36/539* (2013.01); *A61K 36/575* (2013.01); *A61K 36/704* (2013.01); *A61K 36/78* (2013.01); *A61K 36/8888* (2013.01); *A61K 36/8969* (2013.01); *A61P 11/00* (2018.01); *A61P 31/14* (2018.01); *A61K 36/484* (2013.01)

(58) Field of Classification Search
CPC .................................................... A61K 36/714
See application file for complete search history.

*Primary Examiner* — Qiuwen Mi

(74) *Attorney, Agent, or Firm* — SALIWANCHIK, LLOYD & EISENSCHENK

(57) ABSTRACT

The present invention relates to a plant composition, a traditional Chinese medicine composition and use thereof. The plant composition comprises Prepared Monkshood Daughter Root (*Aconitum carmichaelii*), Fragrant Solomonseal Rhizome (*Polygonatum odoratum*), Indian Bread (*Poria cocos*), Pinellia tuber (*Pinellia ternata*), Oriental Wormwood Herb (*Artemisia scoparia*), Scutellaria Root (*Scutellaria baicalensis*), Mongolian Snakegourd Fruit (*Trichosanthes kirilowii*), Magnolia Bark (*Magnolia officinalis*), Heartleaf Houttuynia Herb (*Houttuynia cordata*) and Baked Licorice Root and Rhizome (*Glycyrrhiza glabra*), which is used as a traditional Chinese medicine composition. In addition, the traditional Chinese medicine composition can be used to treat pulmonary embolism or pulmonary fibrosis.

10 Claims, 9 Drawing Sheets
(5 of 9 Drawing Sheet(s) Filed in Color)

(A)

(B)

PLANT COMPOSITION, TRADITIONAL CHINESE MEDICINE COMPOSITION AND USE THEREOF

CROSS-REFERENCE TO RELATED APPLICATION

This application claims the benefit of prior-filed Provisional Application No. 63/262,793, filed on Oct. 20, 2021, in the United States Patent and Trademark Office, the disclosure of which is incorporated herein in its entirety by reference.

BACKGROUND OF THE INVENTION

1. Field of the Invention

The present invention generally relates to a plant composition, traditional Chinese medicine composition and use thereof, in particular to a plant composition, traditional Chinese medicine composition for treating pulmonary embolism or pulmonary fibrosis.

2. Description of the Related Art

Coronavirus appears as an oval shaped particle with a diameter of about 100~120 nm, having an envelope with protruding rod-like spike protein (spike, S protein) anchored on the envelope, resulting the crown-like appearance under an electron microscope, and thus named after the "crown". The envelope of the coronavirus comes from the endoplasmic membrane of infected cells, which is composed of bilayer lipids, having three glycoproteins, namely spike protein (S), M protein (membrane) and E protein (envelope) thereon.

The hosts of coronavirus include a variety of mammals and birds. The most common infection sites are the gastrointestinal tract and respiratory tract. The transmission method is mainly through direct contact with virus-contaminated feces, saliva, or inhalation of particles exhaled by infected animals when they sneeze. It infects the host with a high degree of specificity and causes different symptoms of the disease.

The species of the coronavirus may include the following seven common species, but are not limited thereto: human coronavirus 229E, human coronavirus OC43, human coronavirus NL63, human coronavirus HKU1, Severe Acute Respiratory Syndrome Coronavirus (SARS-CoV), Middle East Respiratory Syndrome Coronavirus (MERS-CoV) and Severe Acute Respiratory Syndrome Coronavirus Type 2 (SARS-CoV-2). Among them, human coronavirus 229E, human coronavirus OC43, human coronavirus NL63, and human coronavirus HKU1 can cause the common cold, while Severe Acute Respiratory Syndrome Coronavirus (SARS-CoV), Middle East Respiratory Syndrome Coronavirus (MERS-CoV) and Severe Acute Respiratory Syndrome Coronavirus Type 2 (SARS-CoV-2) can cause severe respiratory disease, which can lead to death in severe cases. The COVID-19 which caused massive infection in recent years belongs to the Severe Acute Respiratory Syndrome Coronavirus Type 2 (SARS-CoV-2), and had already caused more than 50 million confirmed cases with more than 1.2 million deaths.

There has been a traditional Chinese medicine composition developed by the inventors of the present invention, which is a traditional Chinese medicine composition developed by the National Research Institute of Chinese Medicine, MOHW, namely the Taiwan Qingguan No. 1, or NRICM101. The NRICM101 is composed of Scutellaria root, Heartleaf Houttuynia, Indigowoad root, Trichosanthes Fruit, Fineleaf Nepeta, Peppermint herb, Mulberry leaf, Magnolia Bark, Baked Liquorice root, and Sposhnikovia root and Rhizome.

In order to further alleviate the various infection symptoms caused by coronavirus, the inventors of the present invention further modified some of the plant components on the basis of NRICM1.01, to obtain a novel plant composition, which can be used as a traditional Chinese medicine composition for alleviating various respiratory symptoms caused by coronavirus, especially pulmonary embolism or pulmonary fibrosis.

SUMMARY OF THE INVENTION

Therefore, it is a primary objective of the present invention to provide a plant composition, which can be used as a traditional Chinese medicine composition for alleviating pulmonary embolism or pulmonary fibrosis in patients infected with various types of coronavirus, while also effective in treating other inflammatory diseases.

The plant composition of the present invention comprises Prepared Monkshood Daughter Root (*Aconitum carmichaelii*), Fragrant Solomon seal Rhizome (*Polygonatum odoratum*), Indian Bread (*Poria cocos*), Pinellia tuber (*Pinellia ternata*), Oriental Wormwood Herb (*Artemisia scoparia*), Scutellaria Root (*Scutellaria baicalensis*), Mongolian Snakegourd Fruit (*Trichosanthes kirilowii*), Magnolia Bark (*Magnolia officinalis*), Heartleaf Houttuynia Herb (*Houttuynia cordata*) and Baked Licorice Root and Rhizome (*Glycyrrhiza glabra*), and used as a traditional Chinese medicine composition, named Taiwan Qingguan No. 2, or NRICM102. Wherein, the content of each ingredient of the plant composition is as follows: Prepared Monkshood Daughter Root ((*Aconitum carmichaelii*) 1 parts by weight of an aqueous extract, Fragrant Solomonseal Rhizome (*Polygonatum odoratum*) 1.5 parts by weight of an aqueous extract, Indian Bread (*Poria cocos*) 2.5 parts by weight of an aqueous extract, Pinellia tuber (*Pinellia ternata*) 1.5 parts by weight of an aqueous extract, Oriental Wormwood Herb (*Artemisia scoparia*) 2.5 parts by weight of an aqueous extract, Scutellaria Root (*Scutellaria baicalensis*) 1.5 parts by weight of an aqueous extract, Mongolian Snakegourd Fruit (*Trichosanthes kirilowii*) 2.5 parts by weight of an aqueous extract, Magnolia Bark (*Magnolia officinalis*) 1.5 parts by weight of an aqueous extract, Heartleaf Houttuynia Herb (*Houttuynia cordata*) 5 parts by weight of an aqueous extract, and Baked Licorice Root and Rhizome (*Glycyrrhiza glabra*) 1 parts by weight of an aqueous extract.

When the plant composition is used as a traditional Chinese medicine composition, the method for preparing the traditional Chinese medicine composition comprises mixing the Prepared Monkshood Daughter Root (*Aconitum carmichaelii*), Fragrant Solomonseal Rhizome (*Polygonatum odoratum*), Indian Bread (*Poria cocos*), Pinellia tuber (*Pinellia ternata*), Oriental Wormwood Herb (*Artemisia scoparia*), Scutellaria Root (*Scutellaria baicalensis*), Mongolian Snakegourd Fruit (*Trichosanthes kirilowii*), Magnolia Bark (*Magnolia officinalis*), Heartleaf Houttuynia Herb (*Houttuynia cordata*) and Baked Licorice Root and Rhizome (*Glycyrrhiza glabra*), decocting in water to boiling point, and boil until the water is concentrated to about ¼ volume to obtain a decoction, which is the traditional Chinese medicine composition.

Research have found that the traditional Chinese medicine composition have a positive effect on the treatment of lung injury. The traditional Chinese medicine composition can inhibit the binding between the spike protein of the coronavirus and the type II angiotensin-converting enzyme 2 (ACE2), inhibit the activity of viral 3CL protease, reduce the activation of monocytes and neutrophils, and reduce the expression of various cytokines, thereby blocking viral infection and progression to lung damage caused by pulmonary embolism and pulmonary fibrosis.

With reference to FIG. 1, FIG. 1 is a schematic diagram of the potential pathways of lung injury caused by coronavirus infection and the use of the traditional Chinese medicine composition of the present invention to block viral infection. As shown in the figure, the infection mechanism of coronavirus is through the binding between the spike protein of the coronavirus and the type II angiotensin-converting enzyme 2 (ACE2), which reduces type II alveolar cells and leads to impaired replacement of type I alveolar cells, affects alveolar repair and promotes to induce epithelial mesenchymal transition (EMT), that is, fibrosis. In addition, since the ACE2 is reduced by binding with the spike protein of coronavirus, which in turn overactivates angiotensin-converting enzyme, angiotensin II, and type I alveolar cell receptor axis, will aggravate the tissue destruction effect of inflammatory response, increases the production of plasminogen activator inhibitor-1 (PAI-1), and reduces plasmin activation and fibrinolytic fibrinolysis, which promotes fibrosis.

After being infected by coronavirus, type I alveolar cells, type II alveolar cells and endothelial cells are prompted to release cytokines, resulting in an increase in microvascular permeability, and the adhere and extravasate of neutrophils and monocytes into the alveolar interstitial space. When stimulated by pathogen-related and damage-related molecular patterns (PAMPs and DAMPs), neutrophils and macrophages secrete high levels of cytokines, procoagulants and complements, which further lead to vascular damage and increase the risk of thrombosis.

The key factors of thrombosis are the following:

1. Neutrophil-mediated neutrophil extracellular traps (NETs) and von Willebrand factor (vWF) promote cytokine/viral activation of endothelial cells or macrophages, further lead to aggregated cells in the lungs to produce local platelets, which in turn increases platelet aggregation.
2. Cytokines trigger endothelial cells and macrophages to secrete tissue factor (TF), which stimulates the coagulation cascade and increases the formation of fibrin clots.
3. Excessive activation of angiotensin-converting enzyme, type II angiotensin, and type I alveolar cell receptor axis increases the production of plasminogen activator inhibitor-1 (PAI-1), thereby reducing plasmin activation and fibrinolysis.

By using the traditional Chinese medicine composition of the present invention, the chain effect caused by the binding of type II angiotensin converting enzyme and the spike protein of coronavirus can be blocked, and the apoptosis of type I and/or type II alveolar cells can be reduced, thereby down-regulates the inflammatory response, including the activation of neutrophils and monocytes, the release of cytokines (TNT-$\alpha$, IL-6, MCP-1, etc.) and the expression of inflammatory receptors (TLR4), and can reduce the production of prothrombotic factors (vWF and PAI-1) and fibrotic factors (c-Kit, FN1 and SCF, etc.) to relieve the symptoms of various respiratory infections caused by coronavirus, especially pulmonary embolism and pulmonary fibrosis.

Hereinafter, the actual efficacy of the traditional Chinese medicine composition of the present invention will be proved by specific examples and the obtained experimental data thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The detailed technical features, content and advantages of the present invention will now be described in more details hereinafter with reference to the accompanying drawings that show various embodiments of the invention as follows.

FIG. 2 is a schematic diagram of the inhibitory effect of NRICM102 on the binding of spike proteins of different coronaviruses to ACE2, wherein FIG. 2A is analyzed by BioLayer Interferometry (BLI), and FIG. 2B is analyzed by ELISA for analysis;

DETAILED DESCRIPTION OF THE PREFERRED EMBODIMENTS

Figure 1:
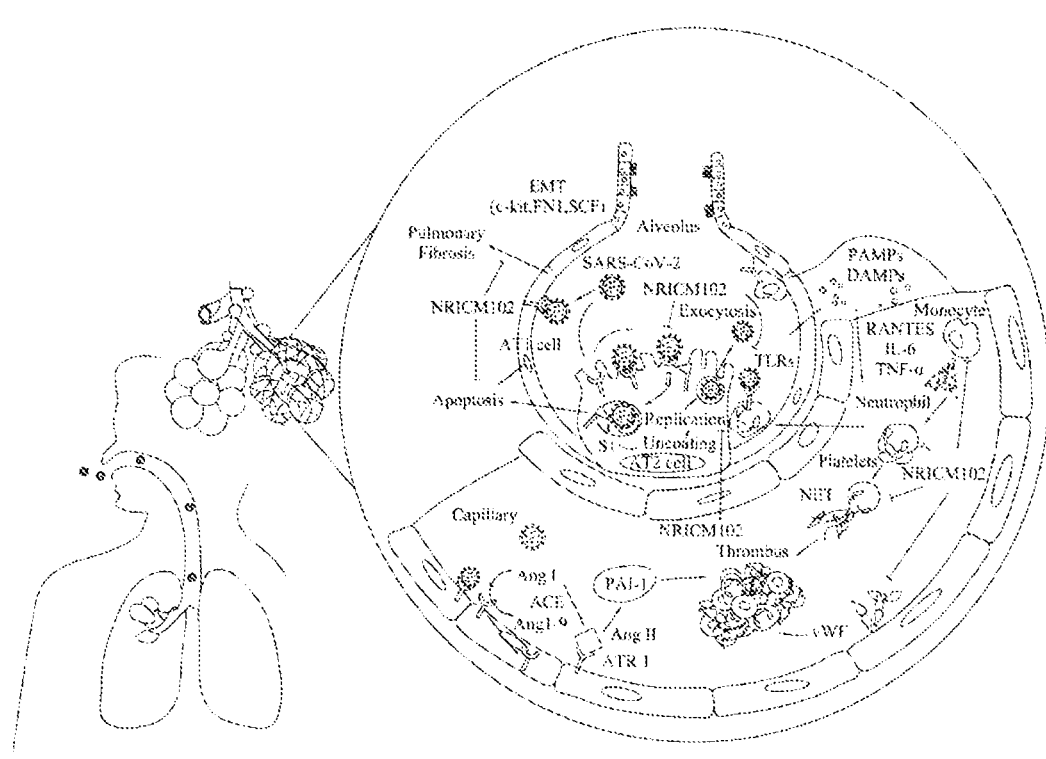
FIG. 1 is a schematic diagram of the potential pathways of lung injury caused by coronavirus infection and the use of the traditional Chinese medicine composition of the present invention to block viral infection.

The technical content of the present invention will become apparent by the detailed description of the following embodiments and the illustration of related drawings as follows. The main purpose of the drawings used herein is only for illustration and auxiliary description, and may not be of real scale and precise configuration in actual implementation of the present invention. Therefore, the scope of the present invention should not be interpreted or limited based on the ratio and configuration relationship of the attached drawings.

Unless otherwise defined, all technical and scientific terms used herein have the same meaning as is commonly understood by a person skilled in the art to which the present invention pertains. It will be further understood that terms such as those defined in commonly used dictionaries should be construed as having meanings consistent with their meanings in the context of the related art and the present invention, and are not to be construed as idealized or excessively formal meaning unless expressly so defined herein.

All numerical values herein are understood to be modified by "about." The term "about" as used herein means to encompass a variation of ±10%.

Materials and Methods

Human bronchial epithelial cells (BEAS-2B) were purchased from Bioresource Collection and Research Center (BCRC, Taiwan); recombinant SARS-CoV-2 spike protein subunit 1 (S1) was purchased from GeneTex International Corporation (UK, product number GTX135817-pro); lipopolysaccharide (*Escherichia coli*, O55:B5) and bleomycin (bleomycin) were purchased from Sigma (USA); the traditional Chinese medicine composition (NRICM102) was prepared by the Chinese Herbal Medicine Pharmacy in Taichung Veterans General Hospital.

Experimental animals were 6-8-week-old male C57BL/6 and ICR mice, purchased from the National Laboratory Animal Breeding and Research Center (Taipei, Taiwan); 14-16-week-old male K18-hACE2 transgenic mice were purchased from Jackson Laboratory and inbred at the Laboratory Animal Center of National Taiwan University College of Medicine. All experimental animals were treated with standard environmental and food conditions, namely 22±1° C., 55±5% humidity, and 12-hour light/dark cycle, with free access to food and water; all experimental animals were randomized into double-blind manner to reduce experimental bias.

Preparation Example 1

Traditional Chinese Medicine Composition and Method for Preparing the Same

The traditional Chinese medicine composition of the present invention comprises Prepared Monkshood Daughter Root (*Aconitum carmichaelii*), Fragrant Solomonseal Rhizome (*Polygonatum odoratum*), Indian Bread (*Poria cocos*), Pinellia tuber (*Pinellia ternata*), Oriental Wormwood Herb (*Artemisia scoparia*), Scutellaria Root (*Scutellaria baicalensis*), Mongolian Snakegourd Fruit (*Trichosanthes kirilowii*), Magnolia Bark (*Magnolia officinalis*), Heartleaf Houttuynia Herb (*Houttuynia cordata*) and Baked Licorice Root and Rhizome (*Glycyrrhiza glabra*), which is NRICM102. The dosages of the ten kinds of Chinese medicine are shown in Table 1 below (the grams (g) of each ingredient herein are exemplary, and the corresponding grams and the corresponding amount of decoction water can be adjusted according to the weight portion ratio).

TABLE 1

| Ingredient of the traditional Chinese medicine composition | content(g) | content (parts by weight of an aqueous extract) |
|---|---|---|
| Prepared Monkshood Daughter Root (*Aconitum carmichaelii*) | 7.50 | 1 |
| Fragrant Solomonseal Rhizome (*Polygonatum odoratum*) | 11.25 | 1.5 |
| Indian Bread (*Poria cocos*) | 18.75 | 2.5 |
| Pinellia tuber (*Pinellia ternata*) | 11.25 | 1.5 |

TABLE 1-continued

| Ingredient of the traditional Chinese medicine composition | content(g) | content (parts by weight of an aqueous extract) |
|---|---|---|
| Oriental Wormwood Herb (*Artemisia scoparia*) | 18.75 | 2.5 |
| Scutellaria Root (*Scutellaria baicalensis*) | 11.25 | 1.5 |
| Mongolian Snakegourd Fruit (*Trichosanthes kirilowii*) | 18.75 | 2.5 |
| Magnolia Bark (*Magnolia officinalis*) | 11.25 | 1.5 |
| Heartleaf Houttuynia Herb (*Houttuynia cordata*) | 37.50 | 5 |
| Baked Licorice Root and Rhizome (*Glycyrrhiza glabra*) | 7.50 | 1 |

The ten kinds of Chinese medicine described in Table 1 are mixed and put into a boiler, add 1.21 L of water for decoction, decocting to boiling point, and boil until the water is concentrated to 300 mL (that is, concentrated to about ¼ volume of water, and the concentrated water is about 40 parts by weight) to obtain a decoction, which is the traditional Chinese medicine composition (NRICM102, which will be used hereinafter).

Embodiment 1

ACE2-Spike Protein Binding and NRICM102 Binding Test

Biolayer interferometric binding events were detected and monitored in real time using a FortéBio Octet Red 96e Biolayer Interferometer (Molecular Device). First, different variants of recombinant SARS-CoV-2 variant RBD proteins (purchased from Sino Biological) were immobilized on the HIS1K sensor tip at a concentration of 100 µg/mL in phosphate buffered saline (PBS) for 600 seconds, followed by blocking the sensor tip with 1% bovine serum albumin (BSA) for 5 minutes; NRICM102 was resuspended in kinetic buffer (PBST, NaCl adjusted to a concentration of 350 mM), and MRICM102 was diluted 5-fold. After that, each sample (recombinant SARS-CoV-2 variant RBD protein of different variants) was added, and the steps of baseline, association and dissociation were used to perform binding tests for 60 seconds, 300 seconds, and 600 seconds in sequence respectively, the sensor tip generates atypical binding events to immobilized protein through non-specific binding effect; then, the correlation signals and curves were aligned to the test data with a 1:1 best fit model using FortéBio data analysis software. In addition, reference sensor subtraction was used to reduce the signal associated with atypical binding events, a set of blank sensors that were individually unloaded with protein were exposed to predetermined conditions.

Results

Figure 2:
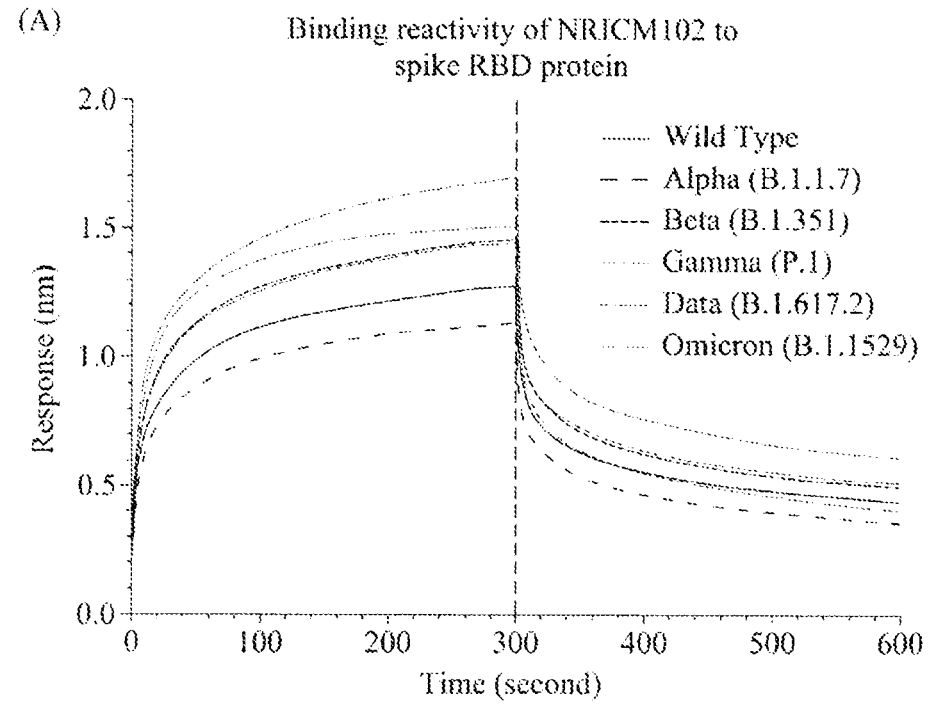
Figure 2:
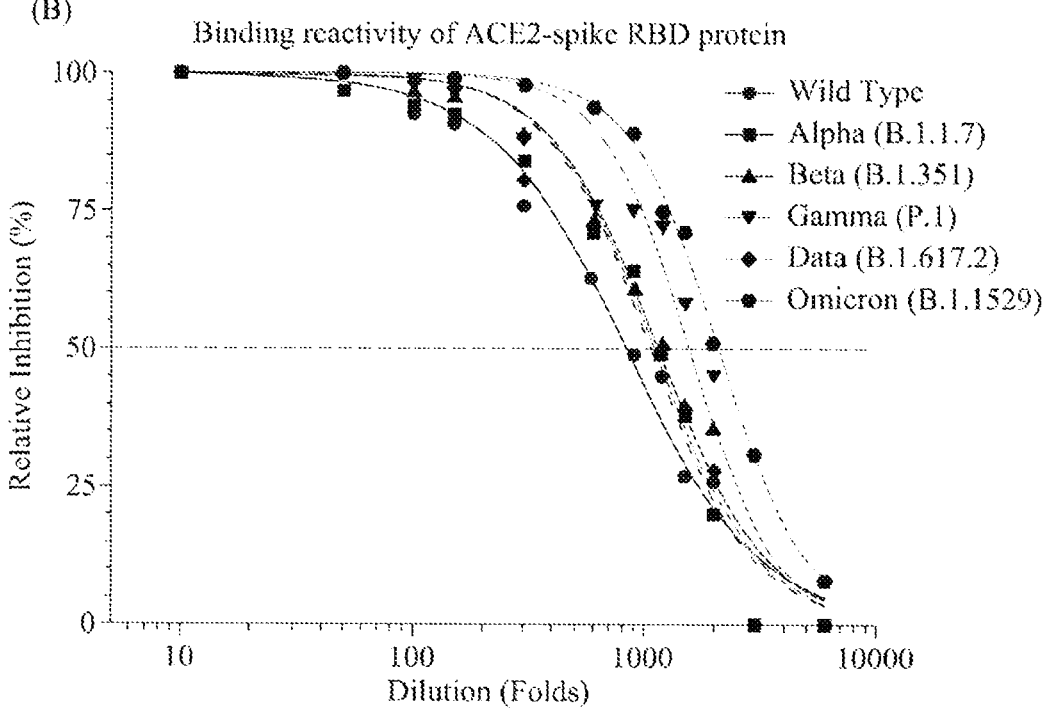

With reference to FIG. 2A, FIG. 2A is analyzed by BioLayer Interferometry (BLI), In the case of administering 5-fold dilution of NRICM102, NRICM102 can bind to the spike proteins of various SARS-CoV-2-related variants, among which NRICM102 has the highest binding activity for the Delta variant, followed by the Omicron variant, the Beta variant, the Gamma variant, Wild Type, and the Alpha variant.

Embodiment 2

ACE2-Spike Protein Inhibition Enzyme-Linked Immunosorbent Assay (ELISA)

Microplates were coated with recombinant SARS-CoV-2 variant RBD protein (0.1~2 μg/well), and after blocking with 1% bovine serum albumin (BSA) for 1 hour at 37° C., NRICM102 was serially diluted (1/10×, 1/50×, 1/100×, 1/150×, 1/300×, 1/600×, 1/900×, 1/1200, 1/1500, 1/2000×, 1/3000×, and 1/6000×) and added to the wells, reacted with recombinant SARS-CoV-2 variant RBD protein at 37° C. After the reaction was completed, hACE2 recombinant protein (0.2 μg/mL) was added to each well and incubated at 37° C. for 40 minutes, and then rabbit anti-human IgG-HRP (purchased from Immunology consultants laboratories, Inc.) was added to each well and incubated for 40 minutes. Then the HRP matrix 3,3',5,5'-tetramethylbenzidine was added to each well for color development, and 1N HCl was used to terminate the reaction after color development was completed, and the signal intensity was quantified at OD 450 nm using a spectrometer. The recombinant SARS-CoV-2 variant RBD spike proteins used include Alpha (B.1.1.7), Beta (B.1.351), Gamma (P.1), Delta (B.1.617.2), Omicron (B.1.1529) and the original wild-type coronavirus.

Results

With reference to FIG. 2B, FIG. 2B shows the effect of the administration of different dilution concentrations of NRICM102 on inhibiting the binding activity of SARS-CoV-2 spike protein and ACE2. As can be seen from the figure, the EC50 of NRICM102 for various SARS-CoV-2 related variants is as follows: 2090-fold dilution for Omicron variant, 1571-fold dilution for Gamma variant, 1151-fold dilution for Beta variant, 1117-fold dilution for Delta variant, 1068-fold dilution for Alpha variant and 833.9-fold dilution for the wild type. From the results above, it can be seen that the antiviral properties of NRICM102 still have significant effects on different SARS-CoV-2 variants.

Embodiment 3

3CL Protease Inhibition Assay

Recombinant SARS-CoV-2 3CL protease (purchased from Pharmtekx, Taipei, Taiwan) was incubated with NRICM102 in reaction buffer (25 mM Tris, 1.00 mM NaCl, 1 mM EDTA, 1 mM DTT, pH 7.3) on ice for 30 min. A luciferase matrix peptide (Dabcyl-KTSAVLQSGFRKME (Edans)-OH, purchased from Kelowna International Scientific Inc., New Taipei City, Taiwan) was then added to induce a proteolytic reaction; Cytation 5 cell imaging multifunctional optical detector (BioTek, Vermont, USA) was used to excite the sample at 355 nm for 1 hour at 37° C., and the reaction was monitored at 538 nm, inhibition was calculated and graphed with GraphPad Prism graphing software.

Results

Figure 3:
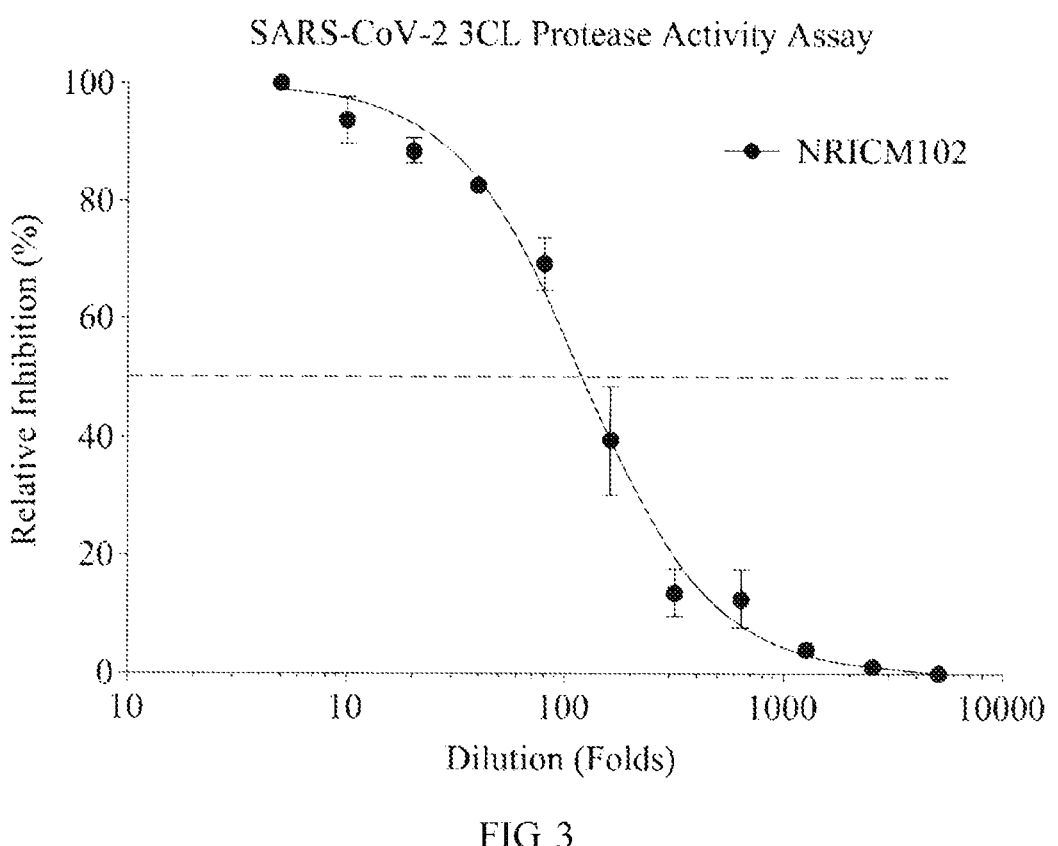
FIG. 3 is a schematic diagram of the inhibitory effect of NRICM102 on the 3CL protease of coronavirus.

With reference to FIG. 3, FIG. 3 is a schematic diagram of the inhibitory effect of NRICM102 on the 3CL protease of coronavirus. As shown in the figure, NRICM102 has a significant inhibitory effect on 3CL protease, and its $IC_{50}$ is 119-fold dilution; therefore, the results prove that NRICM102 has a significant inhibitory effect on 3CL protease activity.

Embodiment 4

Therapeutic Test of Recombinant SARS-CoV-2 Spike Protein Subunit 1 (Spike Protein Subunit 1, S1)-Induced Pulmonary Embolism in K18-hACE2 Mice and Thrombin (Thrombin)-Induced Pulmonary Embolism in ICR Mice After anesthetizing the mice with intraperitoneal injection of xylazine (6 mg/kg) and ketamine (60 mg/kg), a small incision was made in the neck of each mouse, and S1 (400 μg/kg in 2 mL/kg) was dissolved in sterile physiological saline and instilled into the tracheal cavity, the incision was closed after instillation to allow the mice to recover. Mice treated as above were orally administered NRICM102 (1.5 g/kg or 3.0 g/kg) or vehicle (saline, as control group) for 3 consecutive days, then sacrificed the mice to collect lungs; the groups were: Saline control group (Ctrl), S1+saline, S1+NRICM102 (1.5 g) and S1+NRICM102 (3.0 g).

Using lung perfusion detection, mice were perfused with 0.5 mL of 1% Evans blue through the right ventricle; the mouse lungs were then excised and photographed, and the optical density of Evans blue (at OD 620 nm) was measured to estimate the degree of vascular occlusion, and using the iSTAT G3+ detection kit (purchased from Abbott Point of Care Canada Limited, Canada) to measure pulmonary oxygen saturation (SO2%), which is the percentage of oxygen bound to hemoglobin.

Before sacrificing the mice, the distance traveled in a behavioral observation box (60×40×60 cm3) was tracked for 3 minutes to assess the movement activity of the mice, and thereafter an image tracking system (SMART v2.5.21, Panlab, Spain) was used to analyze the results; survival rate was calculated immediately (day 0) and 72 hours (day 3) after administration of S1.

The method for thrombin induced pulmonary embolism in ICR mice was by injecting α-thrombin (50 U/kg, bovine, Sigma-Aldrich, St. Louis, USA) into the vena cava in 100 μL of sterile normal saline to induce acute pulmonary embolism in mice, the groups were: saline control group (Ctrl), thrombin and thrombin+NRICM102 group (3.0 g/kg/day, oral administration for 5 days). The analysis method is the same as the above-mentioned lung perfusion test, pulmonary blood oxygen saturation test and exercise observation; the survival rate is also calculated in the same manner.

Results

Figure 4:
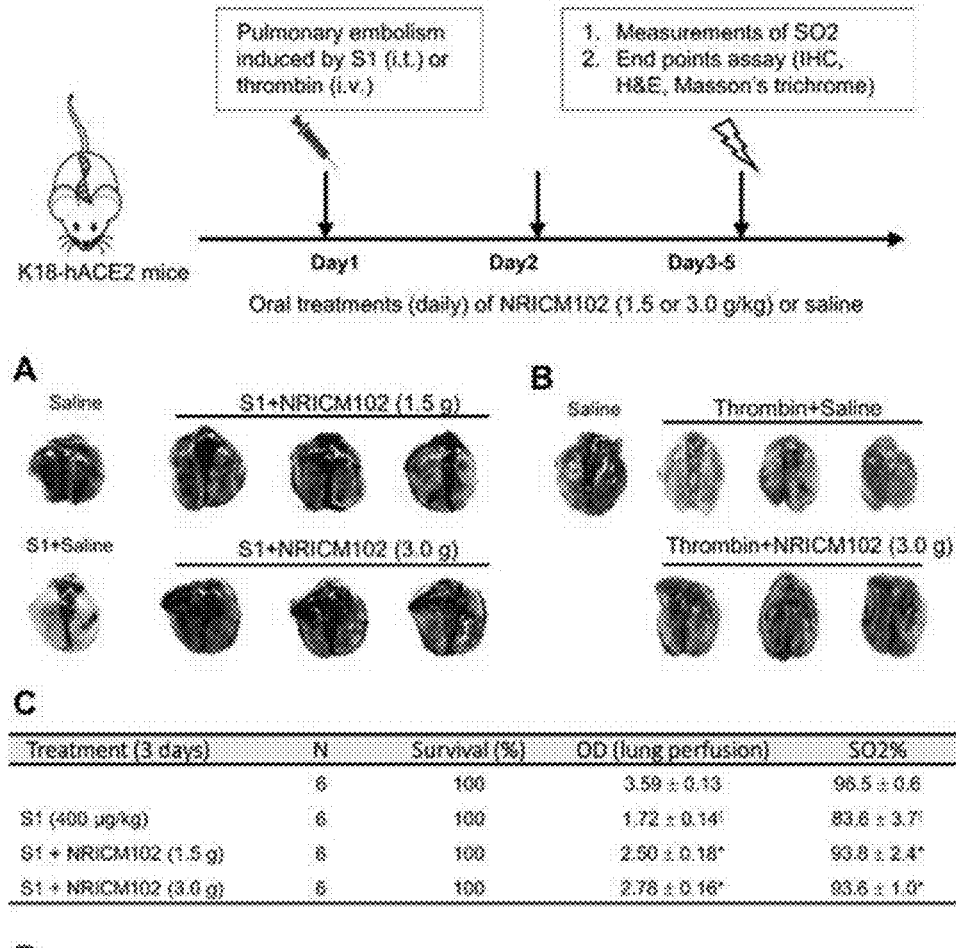
FIG. 4 is a schematic diagram of the therapeutic effect of NRICM102 on pulmonary embolism induced by coronavirus spike protein and thrombin.

With reference to FIG. 4, FIG. 4 is a schematic diagram of the therapeutic effect of NRICM102 on pulmonary embolism induced by coronavirus spike protein and thrombin. From FIGS. 4A and 4C, it can be seen that the spike protein subunit 1 (S1) caused the lung perfusion to decrease by about 52%, from 3.59±0.13 (control group) to 1.72±0.14, and the pulmonary oxygen saturation decreased significantly from 96.5±0.6 to 83.6±3.7% after 3 consecutive days of treatment with different doses of NRICM102, lung perfusion returned to 2.50±0.18 (1.5 g/kg of NRICM102) and 2.78±0.16 (3.0 g/kg of NRICM102), and the pulmonary oxygen saturation of both also recovered to greater than about 93%; thus shows that NRICM1.02 does significantly improve the conditions of the pulmonary embolism induced by S1.

It can also be seen from FIGS. 4B and 4D that thrombin also induced significant pulmonary embolism, killing 40% of the mice within 5 days and causing a decrease in lung perfusion by about 60% (from 3.54±0.04 to 1.38±0.18). After administration of 3.0 g/kg of NRICM102 for 5 consecutive days, the survival rate of mice was significantly improved to 100%, and the pulmonary perfusion recovered to 2.08±0.17 (p<0.05, with statistical significance). However, there were no significant differences in pulmonary oxygen saturation and animal mobility among the groups on day 5.

Therefore, the results can prove that NRICM102 shows significant therapeutic effect on pulmonary embolism caused by coronavirus and thrombin.

Embodiment 5

Therapeutic Test of Bleomycin (BLM)-Induced Lung Injury in C57BL/6 Mice

After the mice were anesthetized by intraperitoneal injection of xylazine (6 mg/kg) and ketamine (60 mg/kg), a small incision was made in the neck of each mouse, and bleomycin (2 U/kg, purchased from Sigma) dissolved in 40 µL of phosphate-buffered saline (PBS) was instilled into the tracheal lumen, and the incision was closed after instillation to allow the mice to recover. Mice treated as above were orally administered NRICM102 (1.5 g/kg or 3.0 g/kg) or vehicle (saline, as control group) daily for 20 consecutive days before sacrifice, and on day 0 to day 21 after bleomycin administration, the mouse body weight and its survival rate were calculated (20% reduction of mouse body weight was selected as the end point of humane sacrifice), and the mouse lung function was measured by conventional plethysmography.

Results

Figure 5:
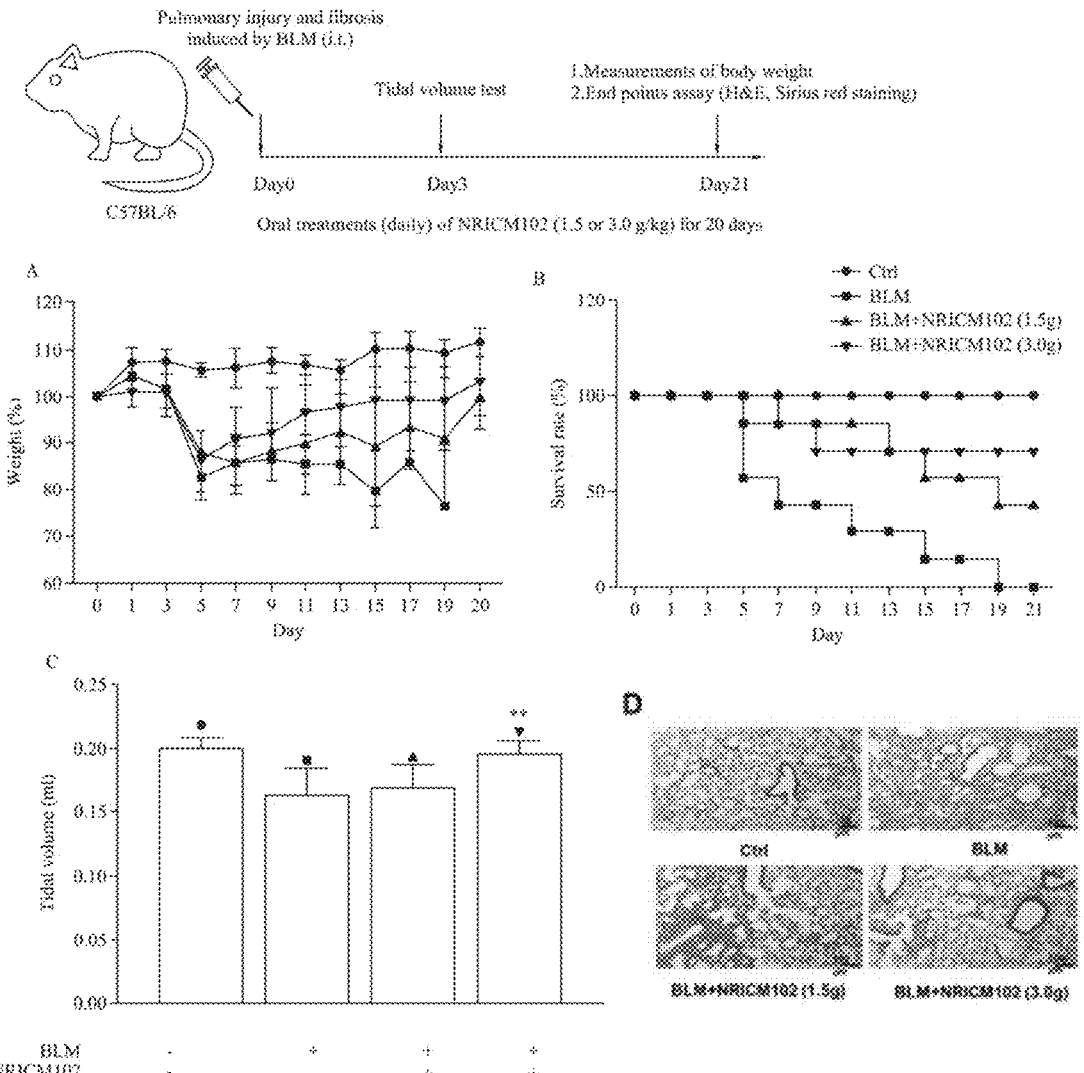
FIG. 5 is a schematic diagram of the therapeutic effect of NRICM102 on bleomycin-induced lung injury.

With reference to FIG. 5, FIG. 5 is a schematic diagram of the therapeutic effect of NRICM1.02 on bleomycin-induced lung injury. As can be seen from FIG. 5A and FIG. 5B, compared with the control group, the mice administered bleomycin (BLM) showed significant weight loss on the 5th day, and the survival rate of the mice decreased significantly from the 7th day. The survival rate dropped to 0% on the 21st day. On the other hand, administration of NRICM102 significantly improved the phenomenon of BLM-induced weight loss, the survival rate of NRICM102 administration of 1.5 g/kg and 3.0 g/kg increased to 42.8% and 71.4%, respectively.

Lung tidal volume of mice was measured 3 days after bleomycin-induced lung injury. As can be seen from FIG. 5C, administration of NRICM102 (3.0 g) significantly reduced bleomycin-induced tidal volume. In addition, through hematoxylin and eosin stain (H&E stain), FIG. 5D shows that the groups administered with NRICM102 have significantly improved the bleomycin-induced lung injury.

Therefore, the results can prove that NRICM102 shows significant therapeutic effect on pulmonary embolism caused by bleomycin.

Embodiment 6

Histopathological and Immunohistochemical Tests

For immunohistochemical (IHC) staining, 15-20 serial sections (about 20-30 µm in thickness) of the same level of lung tissue were collected from different experimental groups for staining, and all tissue sections were fixed, permeabilized and blocked. A primary antibody was randomly selected for specific marker staining (diluted overnight at 4° C. in PBS containing 3% albumin).

Antibodies against S1 RBD (1:100) and citrulline histone H3 (CitH3, NET, 1:50), Ly6G (1:100), MPO (1:100), vWF (1:100), PAI-1 (1:100), PDPN (AT1, 1:100), SFTPC (AT2, 1:100), MIF (1:100) and TLR4 (1:100) were purchased from GeneTex (Irvine, CA, USA), Antibodies against CD11b (1:50) and CD31 (also known as platelet endothelial cell adhesion molecule 1, PECAM-1) were purchased from Abeam (Cambridge, UK). SCF (1:50) and cCasp3 (1:50) antibodies were purchased from Santa Cruz (Santa Cruz Biotechnology, Inc., CA, USA); p-NFκB P65 antibody was purchased from B D Pharmingen (1:50, B D Pharmingen, San Diego, CA, USA), and c-Kit antibody was purchased from Invitrogen (1:200, Invitrogen, Frederick, MD, USA).

After washing the stained sections, all sections were stained with secondary antibodies conjugated to Alexa Fluor® 488, Alexa Fluor® 555 or Alexa Fluor® 647 (all purchased from Cell Signaling Technology Inc., MA, USA). In addition, for counterstaining of DNA in nuclei, all sections on coverslips were mounted in medium containing 4',6-diamidino-2-phenylindole (DAPI) and all correctly stained sections on coverslips were examined using a laser scanning confocal microscope (Zeiss LSM780, Carl Zeiss, Jena, Germany); imaging softwares (Zen 2011, black edition, Carl Zeiss MicroImaging GmbH, 1997-2011) and AlphaEase FC (Alpha Innotech, San Leandro, CA, USA) were used thereafter to sample the portion of the image to be observed from each group at appropriate magnification (30×~11.00×) in 3~5 independent experiments; for the tissue fibrosis test part, the conventional Masson's trichrome staining protocol was followed. The above experiments were conducted to confirm whether administration of NRICM102 can reduce the effect of spike protein subunit 1 (S1) in lung tissue, thereby inhibiting neutrophil infiltration and inflammatory response; and to confirm whether administration of NRICM102 can reduce the expression of prothrombotic factors (vWF and PAI-1) and the formation of NET (CitH3) in lung tissue, thereby inhibiting pulmonary embolism.

Results

Figure 6:
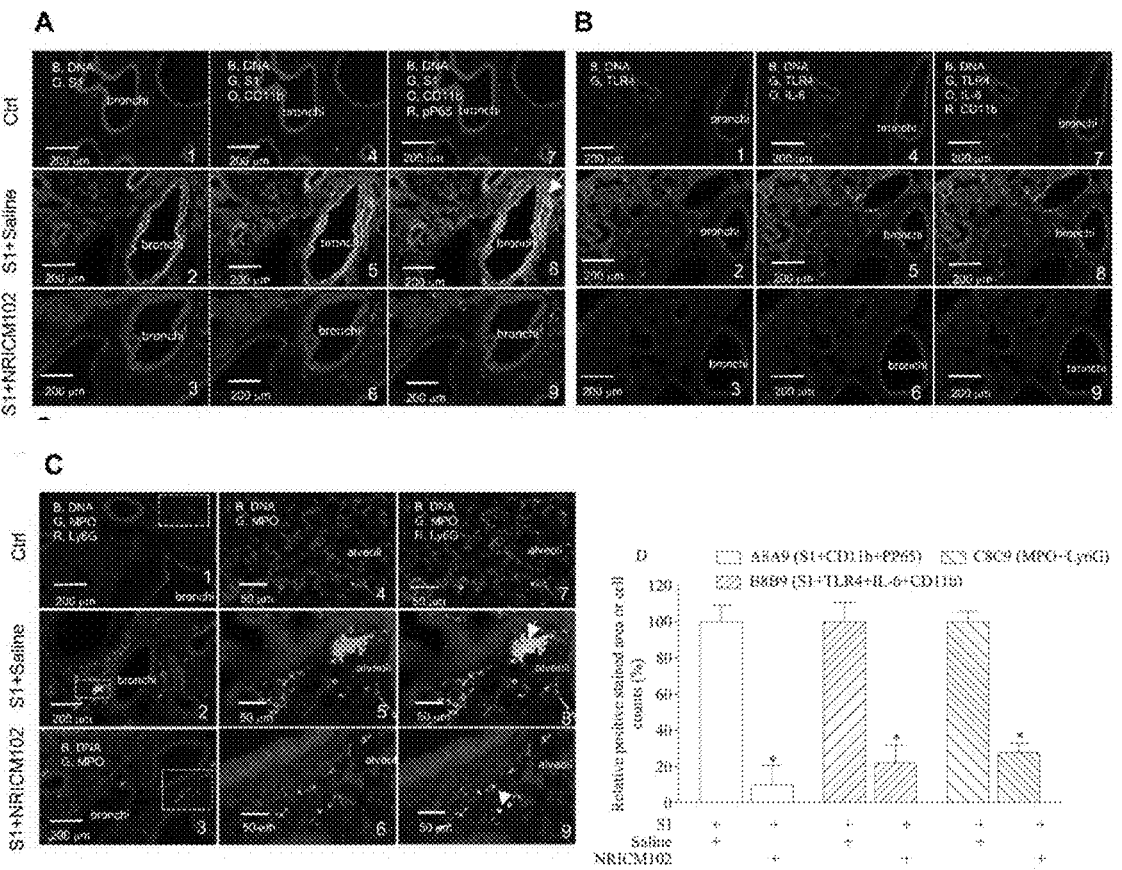
FIG. 6 is a schematic diagram showing the effect of NRICM102 on the changes of spike protein and lung disease (72 hours) in K18-hACE2 mice with lung injury induced by coronavirus spike protein.

With reference to FIG. 6, FIG. 6 is a schematic diagram showing the effect of NRICM1102 on the changes of spike protein and lung disease (72 hours) in K18-hACE2 mice with lung injury induced by coronavirus spike protein. As can be seen from FIGS. 6A to 6C, S1 accumulated to high levels in the bronchi and bronchioles, and the accumulation was accompanied by strong neutrophil and monocyte infiltration (CD11b and Ly6G) and strong inflammatory responses, including the expression of p-NFκB P65, MPO, TLR4 and IL-6; while in the NRICM102-administered group, the accumulation of S1 and the aforementioned inflammatory markers (S1, CD11b, Ly6G p-NTκB P65, MPO, TLR4 and IL-6) level was significantly reduced; in addition, the statistical summary of the selected labeled fluorescent staining (relative staining area or cell count (%)) was shown in FIG. 6D. Therefore, the above experimental results prove that NRICM102 can indeed inhibit neutrophil infiltration and inflammatory response.

Figure 7:
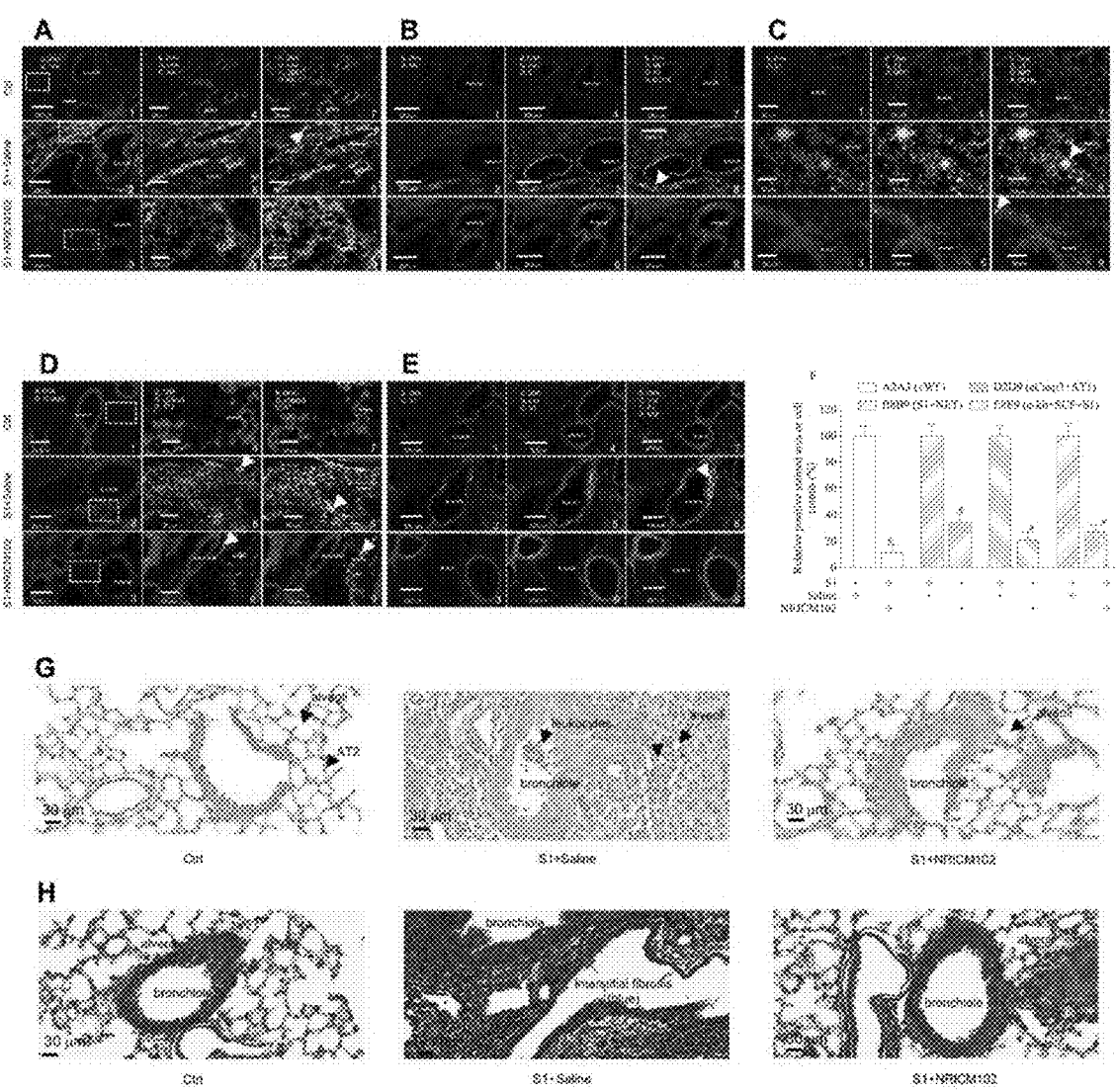
FIG. 7 is a schematic diagram showing the effect of NRICM102 on pulmonary thrombosis, fibrotic factor expression and apoptosis induced by coronavirus spike protein in K18-hACE2 mice.

Furthermore, with reference to FIG. 7, FIG. 7 is a schematic diagram showing the effect of NRICM102 on pulmonary thrombosis, fibrotic factor expression and apoptosis induced by coronavirus spike protein in K18-hACE2 mice. It can be seen from FIG. 7A that after S1 induction, vWF and PAI-1 proteins are highly expressed in lung tissue, and from FIG. 7B and FIG. 7C, it can be seen that strong NET (CitH3) formation and neutrophil infiltration occurred in lung tissue; however, the expression levels of the aforementioned prothrombotic factors (vWF, PAI-1, and NET) were significantly reduced by administration of NRICM102.

Next, the loss of AT1 and AT2 alveolar cells in S1-induced mice was examined by inducing apoptosis; as can be seen in FIG. 7D, significant expression of cleaved caspase 3 and cCasp3 indicates that S1 induces strong apoptosis around lung tissue, while administration of NRICM102 significantly reduces apoptosis (cCasp3) and loss of AT1, AT2 alveolar cells.

Finally, examine whether the expression levels of fibrosis factors (c-Kit and stem cell factor (SCF)) in the lung tissue induced by S1 are increased; FIG. 7E shows that in the lung tissue induced by S1, fibrosis Factors (c-Kit and SCF) were strongly expressed in the peribronchioles, while administration of NRICM102 significantly reduced the expression levels of fibrotic factors. It can also be seen from FIG. 7F and FIG. 7G that the statistical summary of the positive fluorescent staining (relative staining area or cell count (%)) of the selected markers was clearly observed in the S1+saline group, however, it was not observed in the control group (Ctrl) and S1+NRICM102 group; and from the results of Masson's trichrome staining for tissue fibrosis detection in FIG. 7H, it can be seen in the S1+saline group that typical tissue fibrosis (blue part) was clearly observed, but not in the Ctrl group, while the tissue fibrosis effect was significantly reduced in the S1±NRICM102 group. Therefore, the above results prove that NRICM102 can indeed treat pulmonary embolism and pulmonary fibrosis.

Embodiment 7

Monocyte Isolation and Cytokine Array Assay

Peripheral blood mononuclear cells (PBMCs) are isolated from blood samples from healthy donors; that is, PBMCs are isolated from whole blood using Ficoll-Paque™ density gradient centrifugation, and use a typical monocyte isolation kit (Miltenyi Biotec) to isolate monocytes (CD14+ purity 98%) from PBMC, and then treat the isolated monocytes with S1 (100 µg/mL) and NRICM102 for 24 hours; the supernatant (ie, isolated monocytes) was then used for cytokine assays using the Human XL Cytokine Array Kit (Cytokine Array, R&D).

Results

Figure 8:
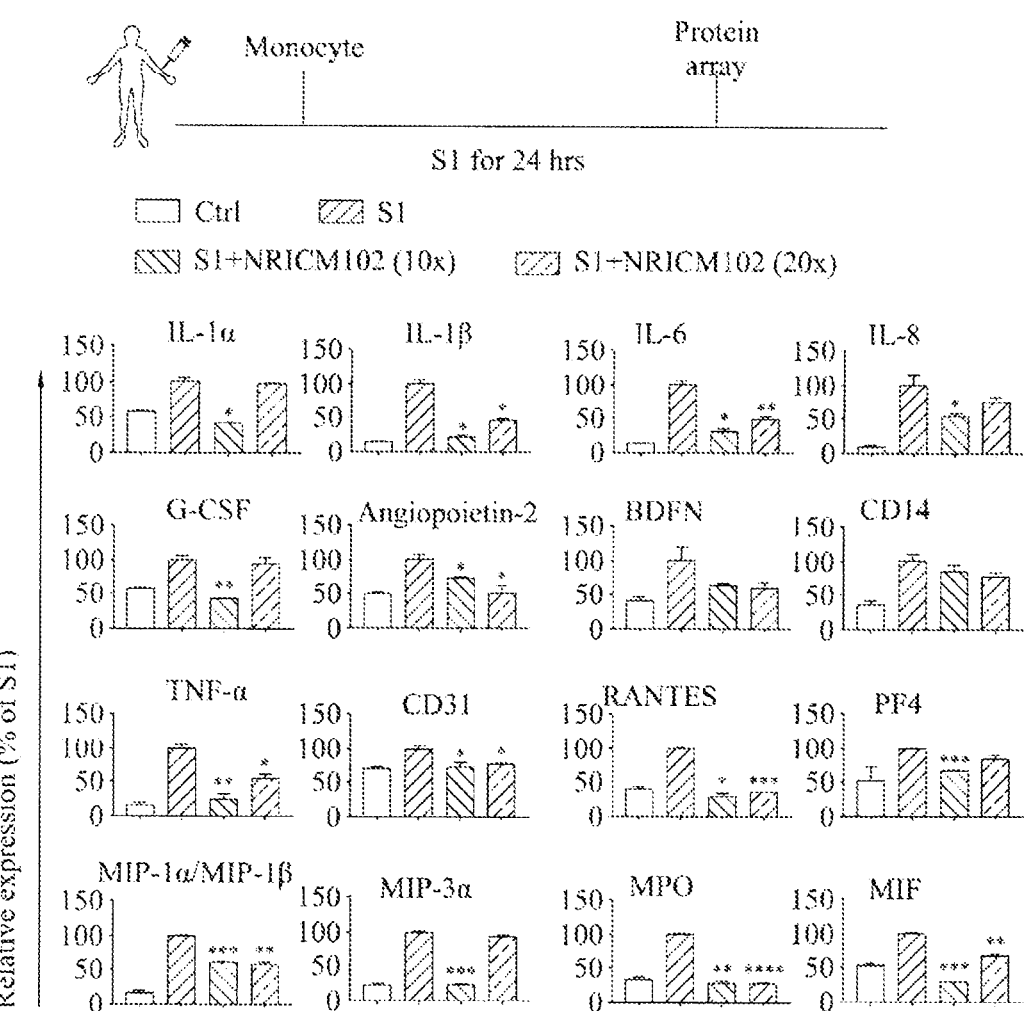
FIG. 8 is a schematic diagram showing the effect of NRICM102 on the expression of cytokines and chemokines induced by coronavirus spike protein in human monocytes.

With reference to FIG. 8, FIG. 8 is a schematic diagram showing the effect of NRICM102 on the expression of cytokines and chemokines induced by coronavirus spike protein in human monocytes. As can be seen from FIG. 8, NRICM102 significantly inhibited the induced expression of various chemokines and cytokines which are factors related to cytokine storm, including INF-α, CD31, RANTES, platelet factor 4 (PF4), IL-1α, IL-1β, IL-6, IL-8, macrophage inflammatory proteins-1α and 1β (MIP-1α, MIP-1β), MIP-3α, myeloperoxidase (MPO), macrophage migration inhibitory factor (MIF), Granular Leukocyte Colony Stimulating Factor (G-CSF) and Angiopoietin-2.

Embodiment 8

Epithelial Mesenchymal Transition (EMT) and Fibroblast to Myofibroblast Transformation (FMT) Assay EMT of bronchial epithelial cells and fibroblast to myofibroblast transformation (FMT) are the key process in the development of pulmonary fibrosis. Epithelial cells which have undergone EMT which subsequently promotes the generation of FMT and fibrogenesis. TGF-β has been reported to induce EMT and FMT which are characterized by the expression of fibronectin (FN1) and alpha smooth muscle actin (α-SMA), respectively. Thus, when EMT occurs in bronchial epithelial cells exposed to TGF-β, fibronectin (FN1) and alpha smooth muscle actin (α-SMA) expression are considered the markers of TGF-β-induced EMT and FMT. In order to evaluate the effect of NRICM102 on EMT of human bronchial epithelial cells (BEAS-2B), the cells were treated with TGF-β or co-treated with TGF-β and NRICM102. And in order to evaluate the effect of NRICM102 on FMT of human fibroblast cells (HFL-1 cells), the cells were treated with TGF-β or co-treated with TGF-β and INRICM102, the processes are as follows:

For EMT assay, BEAS-2B cells were cultured in dishes coated with bovine serum albumin (BSA, purchased from Bionovas), native fibronectin human protein (purchased from Gibco) and bovine collagen I (purchased from (Gibco). The cells were grown at 37° C. under 5% $CO_2$ in bronchial epithelial cell growth basal medium (BEGM, purchased from Lonza). BEAS-2B cells ($6\times10^3$) were seeded in a 96-well black plate (purchased from Thermo Fisher Scientific) and incubated in BEGM for 24 hrs. Then, the cells were stimulated with 10 ng/mL TGF-β (purchased from PeproTech) and incubated for 3 days.

For FMT assay, HFL-1 cells ($6\times10^3$) were seeded in a 96-well black plate (purchased from Thermo Fisher Scientific) and incubated in F-12K (medium with 10% FBS for 24 hrs. The cells were washed 3 times with PBS buffer and starved in F-12K medium with 0.1% FBS for 24 h. Then, the cells were replaced with F-12K medium with 0.5% FBS containing 10 ng/mL TGF-β (purchased from PeproTech) and incubated for 3 days.

The BEAS-2B and HFL-1 cells were fixed with cold methanol (−20° C.) for 30 min at room temperature. Following fixation, permeabilization, and blocking, the BEAS-2B and HFL-1 cells were incubated with a fibronectin antibody (FN1, 1:800 dilution, Cell Signaling) or with alpha smooth muscle actin antibody (α-SMA, 1:800 dilution, Cell Signaling) overnight at 4° C., respectively. After washing, the cells were incubated with Alexa Fluor 488 anti-rabbit IgG (1:1000 dilution, Cell Signaling). The cells were incubated with DAPI (5 µg/mL, purchased from Thermo Fisher Scientific) for nuclear staining. Images were captured with a Cytation 5 Cell Imaging Multi-Optical Detector.

Data analysis was performed using GraphPad Prism software (version 9.0, GraphPad Software, San Diego, CA), and the results of the analysis were expressed as mean±SEM (standard deviation). Statistical analysis involved one-way ANOVA, followed by S-N-K t-test analysis, considered statistically significant at $p<0.05$. In each figure, ** represents $p<0.01$.

Results

Figure 9:
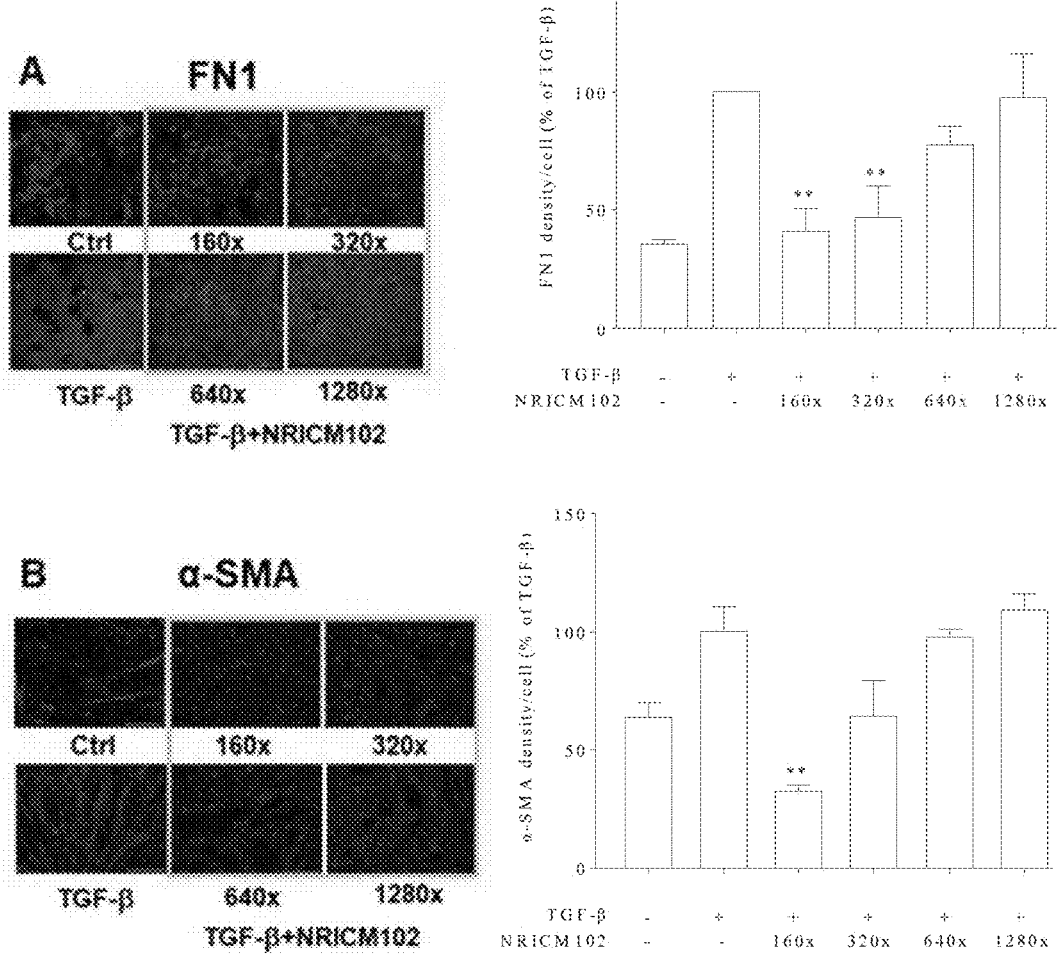
FIG. 9 is a schematic diagram showing the effect of NRICM102 on TGF-$\beta$-induced epithelial-mesenchymal transition (EMT) and fibroblast to myofibroblast transformation (FMT).

With reference to FIG. 9, FIG. 9 is a schematic diagram showing the effect of NRICM1102 on TGF-β-induced epithelial-mesenchymal transition (EMT) and fibroblast to myofibroblast transformation (FMT). The results showed that TGF-β treatment significantly increased the expression of FN1 and α-SMA compared with that in the untreated cells. NRICM102 treatment significantly decreased the expression of FN1 and α-SMA in a dose-dependent manner compared with the expression in the TGF-β treated cells (FIGS. 9A and 9B). These results suggest that NRICM102 exhibited the capability to inhibit the TGF-β induced transition of BEAS-2B cells from bronchial epithelial cells to a mesenchymal-like phenotype and formation of HFL-1 cells from fibroblast to myofibroblast.

In conclusion, the traditional Chinese medicine composition NRICM1.02 (i.e. Taiwan Qingguan No. 2) of the present invention can indeed alleviate various symptoms of respiratory infections caused by coronaviruses, especially pulmonary embolism and pulmonary fibrosis.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A plant composition, wherein the plant composition comprises: Prepared Monkshood Daughter Root, Fragrant Solomonseal Rhizome, Indian Bread, Pinellia tuber, Oriental Wormwood Herb, Scutellaria Root, Mongolian Snakegourd Fruit, Magnolia Bark, Heartleaf Houttuynia Herb and Baked Licorice Root and Rhizome.

2. The plant composition of claim 1, wherein a content of each ingredient of the plant composition is as follows: Prepared Monkshood Daughter Root 1 parts by weight of an aqueous extract, Fragrant Solomonseal Rhizome 1.5 parts by weight of an aqueous extract, Indian Bread 2.5 parts by weight of an aqueous extract, Pinellia tuber 1.5 parts by weight of an aqueous extract, Oriental Wormwood Herb 2.5 parts by weight of an aqueous extract, Scutellaria Root 1.5 parts by weight of an aqueous extract, Mongolian Snakegourd Fruit 2.5 parts by weight of an aqueous extract, Magnolia Bark 1.5 parts by weight of an aqueous extract, Heartleaf Houttuynia Herb 5 parts by weight of an aqueous extract, and Baked Licorice Root and Rhizome 1 parts by weight of an aqueous extract.

3. A traditional Chinese medicine composition, wherein the traditional Chinese medicine composition comprises: Prepared Monkshood Daughter Root, Fragrant Solomonseal Rhizome, Indian Bread, Pinellia tuber, Oriental Wormwood Herb, Scutellaria Root, Mongolian Snakegourd Fruit, Magnolia Bark, Heartleaf Houttuynia Herb and Baked Licorice Root and Rhizome.

4. The traditional Chinese medicine composition of claim 3, wherein a content of each ingredient of the traditional Chinese medicine composition is as follows: Prepared Monkshood Daughter Root 1 parts by weight of an aqueous extract, Fragrant Solomonseal Rhizome 1.5 parts by weight of an aqueous extract, Indian Bread 2.5 parts by weight of an aqueous extract, Pinellia tuber 1.5 parts by weight of an aqueous extract, Oriental Wormwood Herb 2.5 parts by weight of an aqueous extract, Scutellaria Root 1.5 parts by weight of an aqueous extract, Mongolian Snakegourd Fruit 2.5 parts by weight of an aqueous extract, Magnolia Bark 1.5 parts by weight of an aqueous extract, Heartleaf Houttuynia Herb 5 parts by weight of an aqueous extract, and Baked Licorice Root and Rhizome 1 parts by weight of an aqueous extract.

5. A method for treating lung damage, comprising administering a traditional Chinese medicine composition to a subject in need, wherein the traditional Chinese medicine composition comprises: Prepared Monkshood Daughter Root, Fragrant Solomonseal Rhizome, Indian Bread, Pinellia tuber, Oriental Wormwood Herb, Scutellaria Root, Mongolian Snakegourd Fruit, Magnolia Bark, Heartleaf Houttuynia Herb and Baked Licorice Root and Rhizome.

6. The method of claim 5, wherein a content of each ingredient of the traditional Chinese medicine composition is as follows: Prepared Monkshood Daughter Root 1 parts by weight of an aqueous extract, Fragrant Solomonseal Rhizome 1.5 parts by weight of an aqueous extract, Indian Bread 2.5 parts by weight of an aqueous extract, Pinellia tuber 1.5 parts by weight of an aqueous extract, Oriental Wormwood Herb 2.5 parts by weight of an aqueous extract, Scutellaria Root 1.5 parts by weight of an aqueous extract, Mongolian Snakegourd Fruit 2.5 parts by weight of an aqueous extract, Magnolia Bark 1.5 parts by weight of an aqueous extract, Heartleaf Houttuynia Herb 5 parts by weight of an aqueous extract, and Baked Licorice Root and Rhizome 1 parts by weight of an aqueous extract.

7. The method of claim 5, wherein the lung damage includes pulmonary embolism.

8. The method of claim 5, wherein the lung damage includes pulmonary fibrosis.

9. A method for preparing a traditional Chinese medicine composition, comprises:

mixing Prepared Monkshood Daughter Root, Fragrant Solomonseal Rhizome, Indian Bread, Pinellia tuber, Oriental Wormwood Herb, Scutellaria Root, Mongolian Snakegourd Fruit, Magnolia Bark, Heartleaf Houttuynia Herb and Baked Licorice Root and Rhizome, decocting in water to boiling point, and boil until the water is concentrated to about ¼ volume to obtain a decoction, which is the traditional Chinese medicine composition.

10. The method for preparing a traditional Chinese medicine composition of claim 9, wherein a content of each ingredient of the traditional Chinese medicine composition is as follows: Prepared Monkshood Daughter Root 1 parts by weight, Fragrant Solomonseal Rhizome 1.5 parts by weight, Indian Bread 2.5 parts by weight, Pinellia tuber 1.5 parts by weight, Oriental Wormwood Herb 2.5 parts by weight, Scutellaria Root 1.5 parts by weight, Mongolian Snakegourd Fruit 2.5 parts by weight, Magnolia Bark 1.5 parts by weight, Heartleaf Houttuynia Herb 5 parts by weight, and Baked Licorice Root and Rhizome 1 parts by weight.

* * * * *